United States Patent
Graham et al.

(10) Patent No.: US 6,765,113 B2
(45) Date of Patent: Jul. 20, 2004

(54) PRODUCTION OF AROMATIC CARBOXYLIC ACIDS

(75) Inventors: Derek Alexander Graham, Cleveland (GB); Paul Anthony Hamley, Nottingham (GB); Raymond Oliver, Stockton on Tees (GB); Martyn Poliakoff, Nottingham (GB); Duncan Woodcock, Cheshire (GB); Thomas Ilkenhans, Cambridge (GB)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/905,094

(22) Filed: Jul. 13, 2001

(65) Prior Publication Data

US 2002/0028968 A1 Mar. 7, 2002

Related U.S. Application Data

(60) Provisional application No. 60/219,388, filed on Jul. 19, 2000.

(51) Int. Cl.[7] .................. C07C 51/16; C07C 63/14; C07C 51/42
(52) U.S. Cl. ............... 562/413; 562/412; 562/414; 562/415; 562/407; 562/408; 562/409; 562/480; 562/485; 562/486; 562/487; 562/421
(58) Field of Search ................... 562/407–415, 562/421, 480, 485, 486, 487

(56) References Cited

U.S. PATENT DOCUMENTS 5,171,880 A * 12/1992 Masilamani et al. ........ 562/411

FOREIGN PATENT DOCUMENTS

| EP | 0 498 591 | 4/1995 |
|---|---|---|
| EP | 0 502 628 | 10/1996 |
| WO | 98-38150 | 9/1998 |

OTHER PUBLICATIONS

Ding et al. "Supercritical Water Oxidation of NH3 over MnO2?CeO2 catalyst," Ind. Eng. Chem. Res. 1998, vol. 37, p. 1706–1716.*

CAPLUS Abstract, AN 1998:240131, Ding et al. 1998.*

R. L. Holliday, et al., "Organic Synthesis in subcritical water—Oxidation of alkyl aromatics," The Journal of Super-critical Fluids 12 (1998) pp 255–260).

* cited by examiner

Primary Examiner—Shengjun Wang
(74) Attorney, Agent, or Firm—Connolly Bove Lodge and Hutz LLP; Charles E. Krukiel, Esq.

(57) ABSTRACT

A process for the production of an aromatic carboxylic acid comprising contacting in the presence of a catalyst, within a continuous flow reactor, one or more precursors of the aromatic carboxylic acid with an oxidant, such contact being effected with said precursor(s) and the oxidant in an aqueous solvent comprising water under supercritical conditions or near supercritical conditions close to the supercritical point such that said one or more precursors, oxidant and aqueous solvent constitute a substantially single homogeneous phase in the reaction zone, wherein the contact of at least part of said precursor with said oxidant is contemporaneous with contact of said catalyst with at least part of said oxidant.

32 Claims, 8 Drawing Sheets

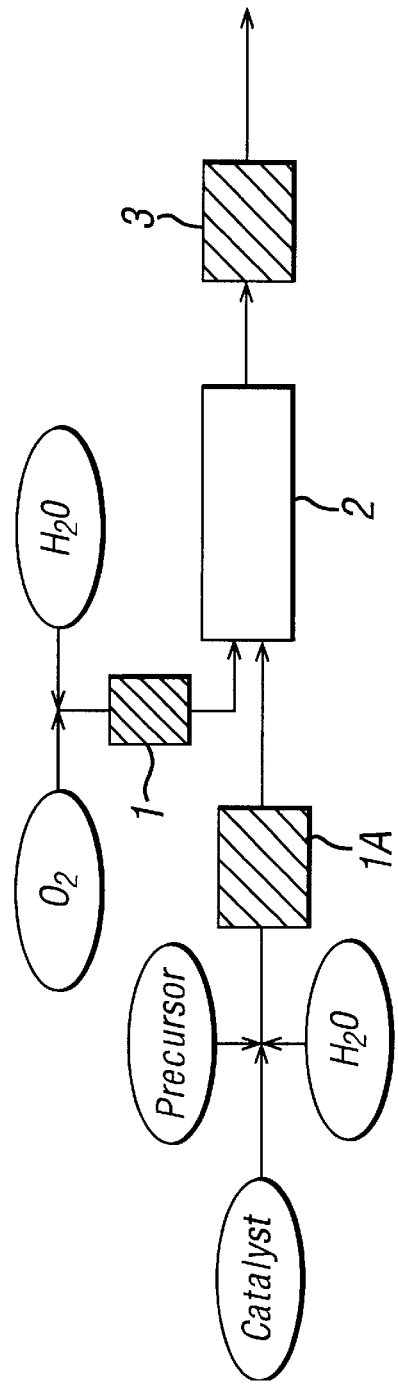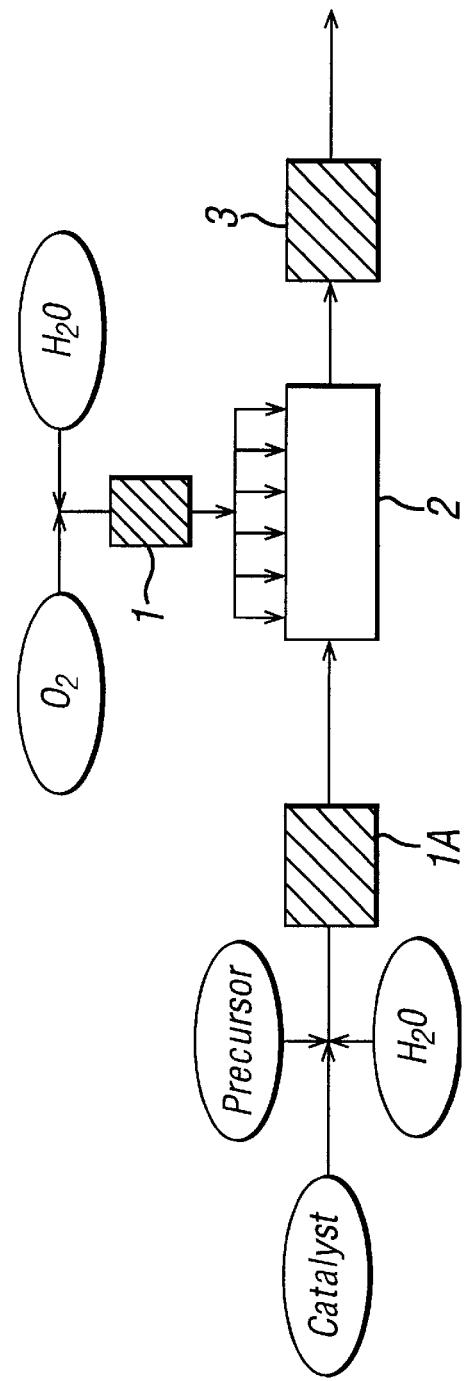

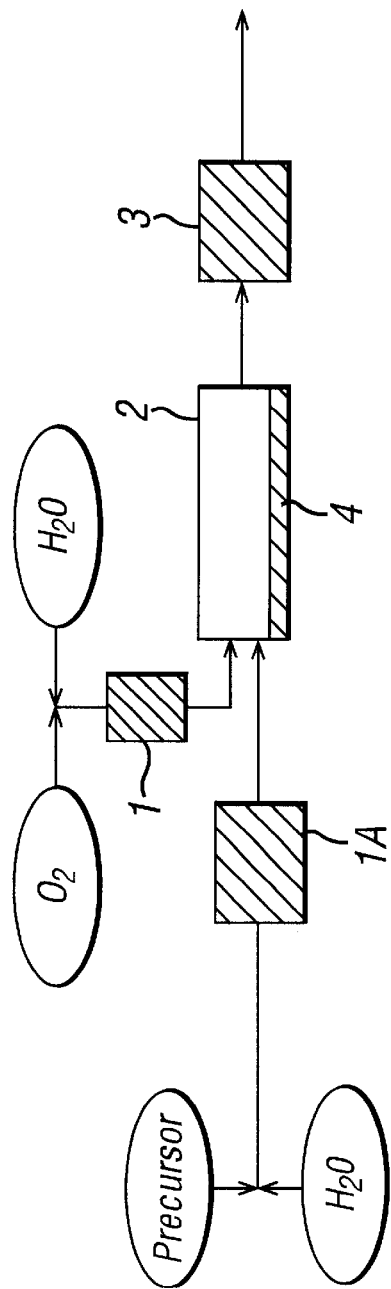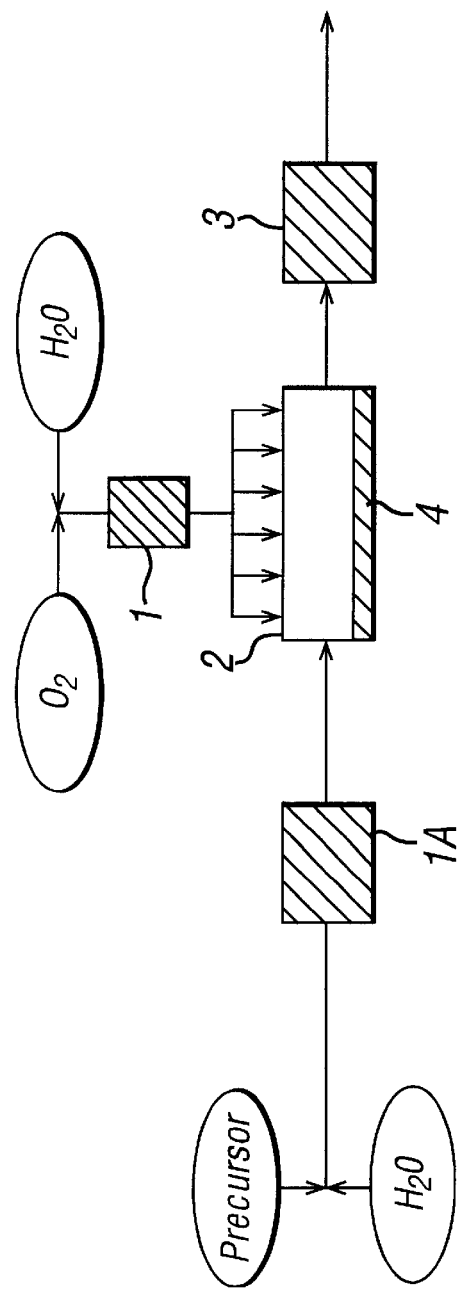

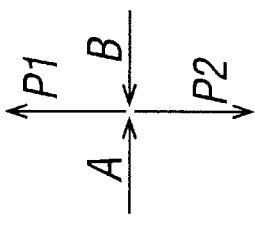
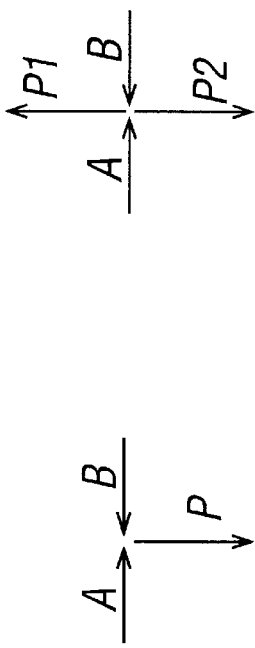
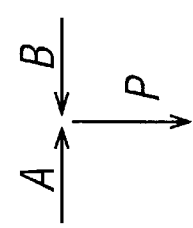
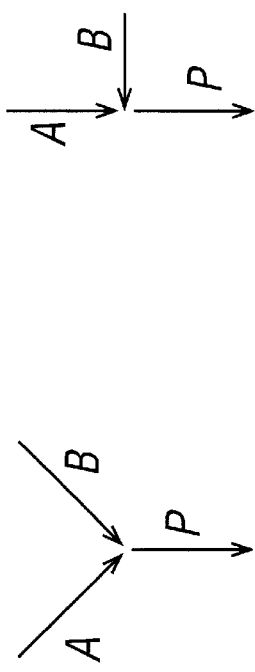
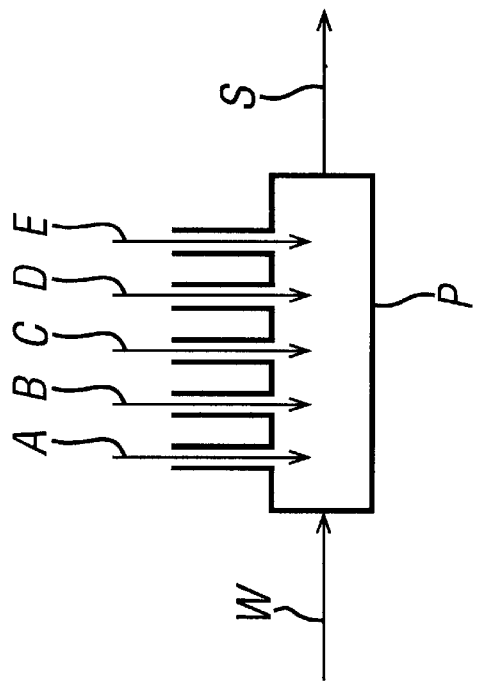
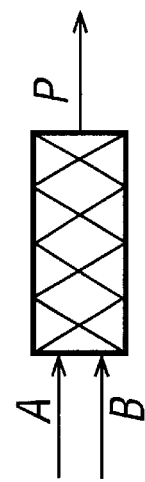

PRODUCTION OF AROMATIC CARBOXYLIC ACIDS

CROSS REFERENCE TO RELATED APPLICATION

This application claims priority benefit of U.S. Provisional Patent Application Serial No. 60/219,388 filed Jul. 19, 2000.

BACKGROUND OF THE INVENTION

This invention relates to a process for the production of aromatic carboxylic acids such as terephthalic acid, isophthalic acid, trimellitic acid, naphthalene dicarboxylic acid and benzoic acid.

Terephthalic acid, by way of an example, is an important intermediate for the production of polyester polymers which are used typically for fibre production and in the manufacture of bottles. Current state-of-the-art technology for the manufacture of terephthalic acid involves the liquid phase oxidation of paraxylene feedstock using molecular oxygen in a lower (e.g. $C_2$–$C_6$) aliphatic monocarboxylic acid, usually acetic acid, in the presence of a dissolved heavy metal catalyst system usually incorporating a promoter, such as bromine. Acetic acid is particularly useful as the solvent since it is relatively resistant to oxidation and increases the activity of the catalytic pathway. The reaction is carried out in a stirred vessel under elevated temperature and pressure conditions, typically 150 to 250° C. and 6 to 30 bara, respectively, and typically produces terephthalic acid in high yield, e.g. at least 95%.

Generally, however, the terephthalic acid obtained is not sufficiently pure for direct use in polyester production since it contains, as major impurities, partially-oxidised intermediates of terephthalic acid, particularly 4-carboxybenzaldehyde (4-CBA), along with various color-forming precursors and colored impurities. In a conventional process used for the production of terephthalic acid, a substantial proportion of the terephthalic acid tends to precipitate as it forms during the course of the reaction and, although it may be below its solubility limit in the solvent under the prevailing conditions, 4-CBA tends to co-precipitate with the terephthalic acid. This relatively crude terephthalic acid, therefore, has to be processed further to secure terephthalic acid of acceptable quality for use in production of high grade polyester. Such further processing typically comprises dissolving the impure terephthalic acid in water at an elevated temperature to produce a solution which is hydrogenated in the presence of a suitable catalyst, e.g. a noble metal catalyst on a carbon support. This hydrogenation step converts the 4-CBA to para-toluic acid while the various color bodies present in the relatively impure terephthalic acid are converted to colourless products. The purified terephthalic acid is then recovered from solution by a series of crystallisation, solid-liquid separation and drying steps. Because para-toluic acid is considerably more soluble in water than terephthalic acid, the former tends to remain in the aqueous mother liquor following crystallisation and solids-liquid separation. A process involving production of crude terephthalic acid and its subsequent purification by hydrogenation is disclosed in, for example, EP-A-0498591 and EP-A-0502628.

In a continuous process described in WO-A-98/38150, relatively high solvent/precursor ratios are employed, and, accordingly, substantially all of the aromatic carboxylic acid produced can be kept in solution thereby minimising co-precipitation of the reaction intermediates in the course of the reaction. As a result, the intermediates remain available for reaction to the desired aromatic carboxylic acid, and the rate of reaction is enhanced for the intermediates compared with a conventional process. By operating the oxidation reaction in this way, it is possible to reduce the extent of contamination of the aromatic carboxylic acid with any aldehyde produced as an intermediate in the course of the reaction. For instance, as mentioned above, in the case of terephthalic acid production by liquid phase oxidation of paraxylene or other precursor, the reaction results in the production of 4-carboxybenzaldehyde as an intermediate. Co-precipitation of 4-CBA with terephthalic acid is largely avoided since the terephthalic acid is not allowed to precipitate during the reaction, at least not to any substantial extent. Moreover, the conditions necessary to achieve this tend to lead to oxidation of intermediates such as 4-CBA to a greater extent to the desired end product.

Although, the process described in WO-A-98/38150 represents a valuable improvement over the prior art, it involves the use of substantial amounts of organic solvent. Although organic solvents, such as acetic acid, are particularly useful in such oxidation processes for the reasons given above, it would in certain situations be desirable to minimise their use. Such organic solvents are relatively costly and, due to environmental restrictions, may require recovery and recycling Furthermore, a proportion of the organic solvent may be 'lost' due to combustion during the oxidation reaction. A further problem with the use of acetic acid is that it is flammable when mixed with air or oxygen under typical reaction conditions in this system.

A further problem with the use of conventional solvents, such as acetic acid, is the low solubility of the oxidant component therein. Thus, where dioxygen is used as the oxidant, the dioxygen is present predominantly as discrete bubbles in the reaction medium with only a small proportion of the dioxygen dissolving in the solvent. To the extent that the reaction between the precursor and the dioxygen results from the dioxygen diffusing from the bubbles into the bulk liquid, the reaction rate is limited by the low solubility of dioxygen in the solvent.

Holliday R. L. et al (J. Supercritical Fluids 12, 1998, 255–260) describe a batch process for the synthesis of, inter alia, aromatic carboxylic acids from alkyl aromatics in a reaction medium of sub-critical water using molecular oxygen as the oxidant. The dielectric constant of water decreases dramatically from a room temperature value of around 80 $C^2/NM^2$ to a value of 5 $C^2/NM^2$ as it approaches its critical point (374° C. and 220.9 bara), allowing it to solubilise organic molecules. As a consequence, water then behaves like an organic solvent to the extent that hydrocarbons, e.g. toluene, are completely miscible with the water under supercritical conditions or near supercritical conditions. Dioxygen is also highly soluble in sub- and super-critical water. The process described by Holliday et al was carried out in sealed autoclaves as a batch reaction.

It is an object of this invention to provide an alternative and improved continuous process for the production of an aromatic carboxylic acid, such as terephthalic acid, wherein substantially all of the aromatic carboxylic acid produced, i.e., intermediates and precursors, are maintained in solution during the reaction, and wherein the need to use an organic material, such as aliphatic monocarboxylic acid, as solvent is eliminated. It is a further object of this invention to provide an alternative and improved continuous process for the production of an aromatic carboxylic acid wherein substantially all of the reactants and product are maintained in a common phase during reaction. It is a further object of this invention to provide a continuous process, having good selectivity and high yield, for the production of an aromatic carboxylic acid by the oxidation of a precursor in sub- or super-critical water.

We have now devised a process which overcomes one or more of the problems previously encountered for the use of supercritical water.

BRIEF SUMMARY OF THE INVENTION

According to the present invention there is provided a process for the production of an aromatic carboxylic acid comprising contacting in the presence of a catalyst, within a continuous flow reactor, one or more precursors of the aromatic carboxylic acid with an oxidant, such contact being effected with said precursor(s) and the oxidant in an aqueous solvent comprising water under supercritical conditions or near supercritical conditions close to the supercritical point such that said one or more precursors, oxidant and aqueous solvent constitute a substantially single homogeneous phase in the reaction zone, wherein the contact of at least part of said precursor with said oxidant is contemporaneous with contact of said catalyst with at least part of said oxidant. Substantially all the aromatic carboxylic acid produced is maintained in solution during the reaction, and thereafter the aromatic carboxylic acid is recovered from the reaction medium.

By employing water under supercritical or near supercritical conditions, the desired aromatic carboxylic acid can be produced without employing aliphatic carboxylic acids, such as acetic acid, as the primary solvent.

The process is carried out with the reactants and the solvent forming a substantially single homogeneous fluid phase in which the components in question are mixed at a molecular level. This is in contrast with existing processes where the dioxygen is present as discrete bubbles in the reaction medium, e.g. acetic acid. To the extent that the reaction between the precursor, e.g. paraxylene, and dioxygen results from dioxygen diffusing from the bubbles into the bulk liquid, the reaction rate of the known process is limited by the solubility of dioxygen in acetic acid, which is not high. The use of water under supercritical or near supercritical conditions as the solvent operates to transform the reaction kinetics, since the concentration of dioxygen in water increases markedly as the supercritical point is approached and exceeded. Moreover, the reaction kinetics are further enhanced by the high temperatures prevailing when the water solvent is under supercritical or near supercritical conditions. The combination of high temperature, high concentration and homogeneity mean that the reaction to convert the precursor(s) to aromatic carboxylic acid can take place extremely rapidly compared with the residence times employed in the production of aromatic carboxylic acids, such as terephthalic acid, by conventional techniques using a crystallising three phase oxidation reactor. Under the conditions described herein according to the invention, the intermediate aldehyde (e.g. 4-CBA in the case of terephthalic acid) can be readily oxidised to the desired aromatic carboxylic acid which is soluble in the supercritical or near supercritical fluid thereby allowing a significant reduction in contamination of the recovered aromatic carboxylic acid product with the aldehyde intermediate. As noted above, in the conventional prior art process of oxidising paraxylene to terephthalic acid, the terephthalic acid is only sparingly soluble in the aliphatic carboxylic acid solvent, and it precipitates in the course of the reaction; because the conversion of 4-CBA to terephthalic acid proceeds relatively slowly, 4-CBA, therefore, tends to co-precipitate with the terephthalic acid, both during the reaction and during the subsequent recovery of the terephthalic acid.

The process of the present invention is particularly advantageous in that it substantially overcomes the problems of autocatalytic destructive oxidation of the precursor and consumption of the catalyst. Furthermore, the process of the present invention involves short residence times and exhibits high yield and good selectivity of product formation.

DETAILED DESCRIPTION OF THE INVENTION

In the process of the invention, the pressure and temperature of the process are selected to secure supercritical or near supercritical conditions. Thus, operating temperatures are typically in the range of from 300° to 480° C., more preferably 330° to 450° C., typically from a lower limit of about 350° to 370° C. to an upper limit of about 370° to about 420° C. Operating pressures are typically in the range from about 40 to 350 bara, preferably 60 to 300 bara, more preferably 220 to 280 bara, and particularly 250 to 270 bara.

By "near supercritical conditions" we mean that the reactants and the solvent constitute a substantially single homogeneous phase; in practice, this can be achieved under conditions below the critical temperature for water. According one embodiment, the term "near supercritical conditions" means that the solvent is at a temperature which is not less than 50° C. below, preferably not less than 35° C. below, more preferably not less than 20° C. below the critical temperature of water at 220.9 bara.

By "continuous flow reactor" as used herein we mean a reactor in which reactants are introduced and mixed and products withdrawn simultaneously in a continuous manner, as opposed to a batch-type reactor. For example, the reactor may be a plug flow reactor, although the various aspects of the invention defined herein are not limited to this particular type of continuous flow reactor.

In the process of the invention, substantially all, and in any event no less than 98% by wt, of the aromatic carboxylic acid produced in the reaction is maintained in solution during the reaction and does not begin to precipitate until the solution leaves the oxidation reaction zone and undergoes cooling.

By carrying out the process in a continuous flow reactor, the residence time for the reaction can be made compatible with the attainment of conversion of the precursor(s) to the desired aromatic carboxylic acid without significant production of degradation products. The residence time of the reaction medium within the reaction zone is generally no more than 10 minutes. However, in practice the reaction runs to completion almost instantaneously as the reactants are mixed, and, therefore, the "residence time" of the reactants in the reaction zone is very short, usually on the order of 2 minutes or less.

The residence time may be controlled so that the precursor is converted rapidly to the corresponding aromatic carboxylic acid with such high efficiency that the aromatic carboxylic acid precipitated from the reaction medium following completion of the reaction contains substantially low levels of aldehyde intermediate, e.g., no more than about 5000 ppm, but even as low as 1500 ppm, and in some cases no more than about 500 ppm aldehyde produced as an intermediate in the course of the reaction (e.g. 4-CBA in the case of terephthalic acid production). Typically, there will be at least some aldehyde present after the reaction, and usually at least 5 ppm.

The reactor system suitable for performing the process of the present invention may be generally configured as described below.

There may be more than one reaction zone in series or in parallel. For instance, where multiple reaction zones in parallel are used, the reactants and solvent may form separate flow streams for passage through the reaction zones and, if desired, the product streams from such multiple reaction zones may be united to form a single product stream. Where more than one reaction zone is used, the conditions, such as temperature, may be the same or different in each reactor. Each reactor may be operated adiabatically or isothermally. Isothermal or a controlled temperature rise may be maintained by heat exchange to define a predetermined temperature profile as the reaction proceeds through the reactor.

In one embodiment of the invention, the heat of reaction is removed from the reaction by heat exchange with a heat-accepting fluid, according to conventional techniques known to those skilled in the art.

In one embodiment, the heat-accepting fluid is passed through one or more flow passages having a wall or walls, the outer surfaces of which are exposed to the reaction medium within the reaction zone. For example, the reactor may be designed in a manner akin to a tube and shell heat exchanger with the reactants and solvent being passed through the shell and the heat-accepting fluid being passed through the tubes internally of the shell.

However, we do not exclude the possibility of effecting the thermal transfer in other ways, for instance by passing the heat-accepting fluid through a jacket arrangement at least partly surrounding the reaction zone. For example, the tube in shell design referred to above may be such that the reactants and solvent flow through the tubes while the heat-accepting fluid flows through the shell.

The heat-accepting fluid may traverse the reaction zone in countercurrent and/or co-current relation with the reaction medium flowing through the reaction zone. Conveniently the passage or passages conducting the heat-accepting fluid are arranged to extend internally of the reactor.

Advantageously, the heat-accepting fluid following heat exchange with the reaction medium is processed to recover thermal, mechanical and/or electrical energy. The power recovered may in part be employed to pressurise air or oxygen to be supplied as oxidant to the process, e.g. by driving a compressor suitable for this purpose. For example, heat transferred to the heat-accepting fluid may be converted to mechanical or electrical energy in a power recovery system. One approach is to use the heat-accepting fluid to raise high pressure steam which can then be superheated and supplied to a steam turbine to recover power. Sufficient power may be recovered to allow export from the plant for use elsewhere.

Conveniently the heat-accepting fluid comprises water.

The heat-accepting fluid may be preheated prior to traversing the reaction zone, and such preheating may be effected by heat exchange with the product stream resulting from the oxidation reaction.

The oxidant in the process of the invention is preferably molecular oxygen, e.g. air or oxygen enriched air, but preferably comprises gas containing oxygen as the major constituent thereof, more preferably pure oxygen, or oxygen dissolved in liquid. The use of air is not favoured, although not excluded from the scope of the invention, since large compression costs would arise and offgas handling equipment would need to cope with large amounts of offgas owing to the high nitrogen content of air. Pure oxygen or oxygen enriched gas on the other hand permits use of a smaller compressor and smaller offgas treatment equipment. The use of dioxygen as the oxidant in the process of the invention is particularly advantageous since it is highly soluble in water under supercritical or near supercritical conditions. Thus, at a certain point, the oxygen/water system will become a single homogeneous phase.

Instead of molecular oxygen, the oxidant may comprise atomic oxygen derived from a compound, e.g. a liquid phase compound at room temperature, containing one or more oxygen atoms per molecule. One such compound for example is hydrogen peroxide, which acts as a source of oxygen by reaction or decomposition as described by Lin, Smith, et al (International Journal of Chemical Kinetics, Vol 23, 1991, p971).

The process of the invention is carried out in the presence of an oxidation catalyst. The catalyst may be soluble in the reaction medium comprising solvent and the aromatic carboxylic acid precursor(s) or, alternatively, a heterogeneous catalyst may be used. The catalyst, whether homogeneous or heterogeneous, typically comprises one or more heavy metal compounds, e.g. cobalt and/or manganese compounds, and may optionally include an oxidation promoter. For instance, the catalyst may take any of the forms that have been used in the liquid phase oxidation of aromatic carboxylic acid precursors such as terephthalic acid precursor(s) in aliphatic carboxylic acid solvent, e.g. bromides, bromoalkanoates or alkanoates (usually C1–C4 alkanoates such as acetates) of cobalt and/or manganese. Compounds of other heavy metals, such as vanadium, chromium, iron, molybdenum, a lanthanide such as cerium, zirconium, hafnium, and/or nickel may be used instead of cobalt and/or manganese. Advantageously, the catalyst system will include manganese bromide ($MnBr_2$). The oxidation catalyst may alternatively or additionally include one or more noble metals or compounds thereof, e.g. platinum and/or palladium or compounds thereof, for example in highly divided form or in the form of a metal sponge. The oxidation promoter where employed may be in the form of elemental bromine, ionic bromide (e.g. HBr, NaBr, KBr, $NH_4Br$) and/or organic bromide (e.g. bromobenzenes, benzyl-bromide, mono- and di-bromoacetic acid, bromoacetyl bromide, tetrabromoethane, ethylene-di-bromide, etc.). Alternatively the oxidation promoter may comprise a ketone, such as methylethyl ketone, or aldehyde, such as acetaldehyde.

Where the catalyst is in heterogeneous form, it may be suitably located within the reaction zone so as to secure contact between the continuously flowing reaction medium and the catalyst. In this event, the catalyst may be suitably supported and/or constrained within the reaction zone to secure such contact without unduly constricting the flow cross-section. For instance, the heterogeneous catalyst may be coated on or otherwise applied to, or embodied in, static elements (e.g. elements forming an openwork structure) positioned of within the reaction zone so that the reaction medium flows over the same. Such static elements may additionally serve to enhance mixing of the reactants as they pass through the reaction zone. Alternatively the catalyst may be in the form of mobile pellets, particles, finely divided form, metal sponge form or the like with means being provided if necessary to confine the same to the reaction zone so that, in operation, the catalyst pellets etc become suspended or immersed in the reaction medium flowing through the reaction zone. The use of a heterogeneous catalyst in any of these ways confers the advantage of being able to confine the catalysis effect to a well-defined zone so that, once the reaction medium has traversed the zone, further oxidation takes place at a reduced rate or may be significantly suppressed.

The support for the oxidation catalyst can be less catalytically active or even inert to the oxidation reaction. The support may be porous and typically has a surface area, including the area of the pores on the surface, of at least 25 $m^2/gm$ to 250 $m^2/gm$, e.g. from 50 $m^2/gm$ to 200 $m^2/gm$, with a surface area of about 80 $m^2/gm$ to about 150 $m^2/gm$ being preferred. The catalyst support materials should be substantially corrosion resistant and substantially oxidation resistant under the conditions prevailing. The support component of the oxidation catalyst may be pure or a composite of materials, the latter being employed for example to impart desired chemical or physical characteristics to the catalyst. In a preferred embodiment, the catalyst support material comprises zirconium dioxide.

The oxidation reaction is initiated by heating and pressurising the reactants followed by bringing the heated and pressurised reactants together in a reaction zone. This may be effected in a number of ways with one or both of the reactants being admixed with the aqueous solvent prior to or after attainment of supercritical or near supercritical conditions, such admixture being effected in such a way as to maintain the reactants isolated from one another until brought together in the reaction zone.

In the continuous process of the present invention, the reactor system is configured such that the contact between the oxidant and at least part, and preferably substantially all, of the precursor is made at the same point in the reactor system as the contact between the catalyst and at least part, and preferably substantially all, of the oxidant.

In a first embodiment, the oxidant is mixed with the aqueous solvent after the latter has been heated and pressurised to secure the supercritical or near supercritical state, with suitable pressurisation and, if desired, heating, of the oxidant prior to mixing with the aqueous solvent. The precursor is subjected to pressurisation and, if desired, heating. In the case of a process using a homogeneous catalyst, the catalyst component is subjected to pressurisation and, if desired, heating. The precursor, the catalyst and the oxidant/solvent mixture are then contacted simultaneously. In the case of a process using a heterogeneous catalyst, the precursor is contacted with the oxidant/solvent mixture in the presence of the catalyst.

In a second embodiment of the invention, the precursor is mixed with the aqueous solvent after the latter has been heated and pressurised to secure the supercritical or near supercritical state, with suitable pressurisation and, if desired, heating, of the precursor prior to mixing with the aqueous solvent. In one arrangement, a homogenous catalyst component, after pressurisation and optional heating, is contacted with the aqueous solvent simultaneously with the contacting of the precursor with the aqueous solvent. In an alternative arrangement, a heterogeneous catalyst is used and confined to the reaction zone as described herein. The oxidant after pressurisation and, if desired, heating, is mixed with aqueous solvent after the latter has been heated and pressurised to secure the supercritical or near supercritical state. In the case of a process using a homogeneous catalyst, the oxidant/aqueous solvent mixture is then contacted with the mixture comprising the precursor, catalyst and aqueous solvent. In the case of a process using a heterogeneous catalyst, the oxidant/aqueous solvent mixture is contacted in the reaction zone, i.e. in the presence of the heterogeneous catalyst, with the mixture comprising the precursor and aqueous solvent.

Contact of the various streams may be effected by way of separate feeds to a device in which the feeds are united to form a single homogeneous fluid phase thus allowing the oxidant and precursor to react. The device in which the feeds are united may for instance have a Y, T, X or other configuration allowing separate feeds to be united in a single flow passage forming the continuous flow reactor, or in some circumstances multiple flow passages forming two or more continuous flow reactors. The flow passage or passages in which the feeds are united may comprise a section of tubular configuration with or without internal dynamic or static mixing elements.

In a preferred embodiment, in-line or static mixers are advantageously used to ensure rapid mixing and homogeneity, for example to promote dissolution of oxidant into the aqueous solvent and the formation of a single phase.

The oxidant feed and the precursor feed may be brought together at a single location or the contact may be effected in two or more stages so that at least part of one feed or of both feeds are introduced in a progressive manner, e.g. via multiple injection points, relative to the direction of flow through the reactor. For instance, one feed may be passed along a continuous flow passage into which the other feed is introduced at multiple points spaced apart lengthwise of the continuous flow passage so that the reaction is carried out progressively. The feed passed along the continuous flow passage may include the aqueous solvent as may the feed introduced at multiple positions.

Similarly, the addition of catalyst, particularly homogenous catalyst, may be effected in a progressive manner, e.g. via multiple injection points, relative to the direction of flow through the reactor.

In one embodiment, the oxidant is introduced to the reaction at two or more locations. Such locations are conveniently so positioned relative to the bulk flow of solvent and reactants through the oxidation zone that oxidant is introduced to the reaction at an initial location and at least one further location downstream of said initial location.

After traversing the continuous flow reactor, the reaction mixture comprises a solution of aromatic carboxylic acid. In contrast with conventional prior art processes, substantially the entire amount of aromatic carboxylic acid produced in the reaction is in solution at this stage. The solution may also contain catalyst (if used), and relatively small quantities of by-products such as intermediates (e.g. p-toluic acid and 4-CBA in the case of terephthalic acid), decarboxylation products such as benzoic acid and degradation products such as trimellitic anhydride and any excess reactants. The desired product, aromatic carboxylic acid, such as terephthalic acid, may be recovered by causing or allowing the aromatic carboxylic acid to crystallise from the solution in one or more stages followed by a solids-liquid separation in one or more stages.

Another aspect of the invention is concerned with cooling of the product stream resulting from the oxidation reaction. In this aspect of the invention, the product stream is subjected to a solids-liquid separation to recover the aromatic carboxylic acid and the mother liquor (which may but need not necessarily contain dissolved catalyst components) is recycled to the oxidation reaction zone.

Preferably prior to re-introduction into the oxidation reaction zone, the mother liquor is heated by heat exchange with the product stream thereby cooling the latter.

One or both reactants may be admixed with the mother liquor recycle stream or separate mother liquor recycle streams prior to re-introduction of the mother liquor into the reaction zone and the mother liquor recycle stream (or at least that fraction or those fractions thereof to be combined with the reactant or reactants) may be heated and pressurised to secure supercritical/near supercritical conditions before being admixed with the reactant or respective reactant.

Where the mother liquor is heated by heat exchange with the product stream before re-introduction into the oxidation zone, the reactant or reactants may be admixed with the mother liquor stream or a respective mother liquor stream prior to or after such heat exchange with the product stream.

The invention will now be described further by way of example only with reference to the accompanying drawings in which:

FIGS. 1A and 1B are schematic flowsheets illustrating the basic arrangement described for the first embodiment above, wherein FIG. 1A illustrates use of a homogeneous catalyst, and FIG. 1B illustrates use of a heterogeneous catalyst.

FIGS. 2A–2D are schematic flowsheets illustrating the basic arrangement described for the second embodiment above, wherein FIGS. 2A and 2B illustrate use of a homogeneous catalyst and FIGS. 2C and 2D illustrate use of a heterogeneous catalyst. In FIGS. 2B and 2D, the oxidant is introduced in a progressive manner along the reaction zone at multiple injection points.

FIGS. 4A, 4B, 4C, 4D and 5 illustrate various premixer configurations that may be employed to effect mixing of at least one of the reactants with the aqueous solvent;

FIG. 6 is a schematic view illustrating multiple stage injection of oxidant;

Figure 1A:
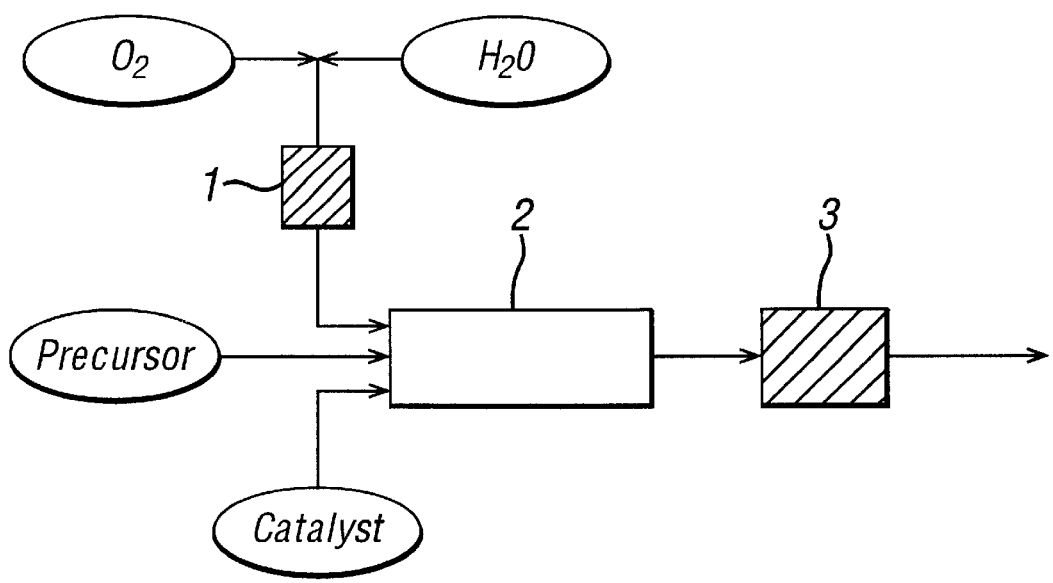

Referring to FIG. 1A, dioxygen, after pressurisation, is mixed with water after the water has been heated and the mixture pressurised and optionally further heated in preheater 1 to achieve the supercritical state. The precursor and catalyst are added, after pressurisation, to the $O_2$/water stream at the beginning of or immediately before the reactor 2 and the mixture passed through the reactor. Upon exiting the reactor, the stream is cooled and depressurised at the back-pressure regulator 3. The products are carried out in a stream of cooled water. In corresponding FIG. 1B, the catalyst is already present as a heterogeneous catalyst within the reactor.

Referring to FIGS. 2A and 2B, the precursor and catalyst, after pressurisation are added to water after the water has been pressurised and optionally heated, and optionally further heated in preheater 1A to achieve the supercritical state. The dioxygen gas, after pressurisation is mixed with water at a supercritical state and optionally further heated in preheater 1. In FIG. 2A, the two streams are mixed at the beginning of or immediately before the reactor 2 and the mixture passed through the reactor. In FIG. 2B, the $O_2$/water stream is added to the reactor in a progressive manner at multiple injection points. Upon exiting the reactor, the stream is cooled and depressurised at the back pressure regulator 3. The products are carried out in a stream of cooled water. In corresponding FIGS. 2C and 2D, the catalyst is already present as a heterogeneous catalyst within the reactor.

Figure 3:
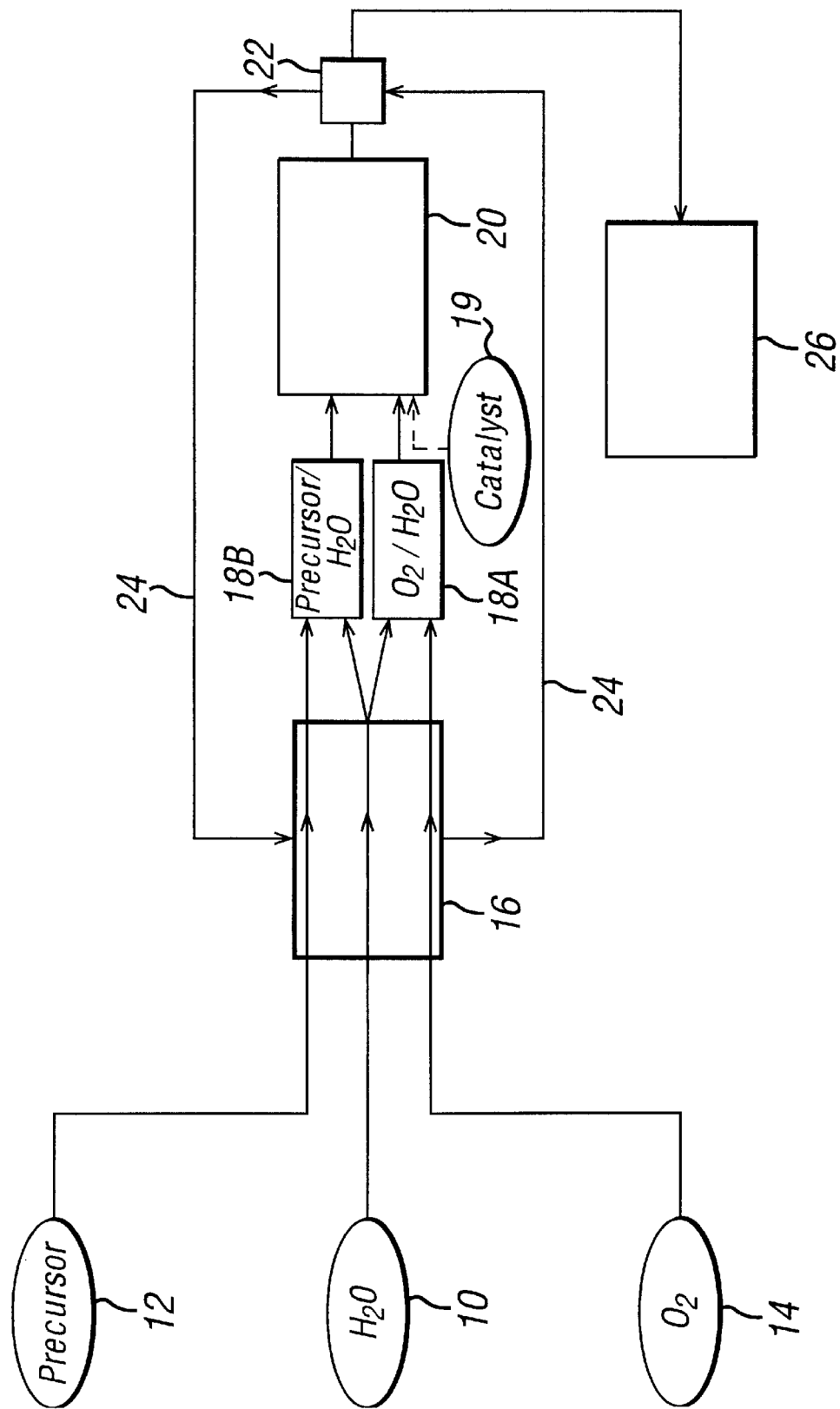
FIG. 3 is a schematic flowsheet illustrating in more detail an arrangement wherein the precursor is added to a premixed stream of oxygen and water (i.e. an arrangement according to the process illustrated in FIG. 1A or 1B).

Referring to FIG. 3, feedstock components comprising water, paraxylene and dioxygen gas are pressurised to operating pressure and continuously supplied from respective sources 10, 12 and 14 through a preheater 16 where the components are heated to a temperature of 300° to 480° C., more preferably 330° to 450° C., typically from about a lower limit of about 350° to 370° C. to an upper limit of about 370° to about 420° C., the pressure and temperature being selected in order to secure supercritical or near supercritical conditions. Part of the heat used to preheat the feedstock components may be derived from the exotherm produced in the course of the subsequent reaction between the terephthalic acid precursor (i.e. paraxylene in this embodiment) and the oxidant. Heat from other sources may be, for example, in the form of high pressure steam and/or heating may be effected by direct fired heating of the water stream. The heat of reaction may be recovered in any suitable manner, e.g. by means of heat exchange between the fluid following reaction and a suitable heat-accepting fluid such as water. For instance, the heat-accepting fluid may be arranged to flow in heat exchange relation, countercurrently and/or co-currently, with the reactants and solvent passing through the reaction zone. The passage or passages along which the heat-accepting fluid flows in traversing the reaction zone may be external to the reaction zone and/or may extend internally through the reaction zone. Such internally extending flow passage(s) may for instance extend generally parallel with and/or transversely of the general direction of flow of the reactant/solvent through the reaction zone. For example, the heat-accepting fluid may traverse the reaction zone by passage through one or more coiled tubes located within the interior of the reactor. The enthalpy of reaction can be used to recover power via a suitable power recovery system such as a turbine; for instance the heat-accepting fluid, e.g. water, can be used to raise high pressure saturated steam at for example temperature and pressure of the order of 300° C./100 bara which, in turn, can be superheated by external heat and fed to a high efficiency condensing steam turbine to recover power. In this way, the reactor can be maintained at an optimum temperature and effective energy efficiency can be achieved. In an alternative approach, the reactor may be operated under adiabatic conditions and a suitably high rate of water flow through the reaction zone may be employed in order to constrain the temperature rise across the reactor in operation. If desired, a combination of both approaches may be used, i.e. recovery of the enthalpy of reaction via a heat-accepting fluid coupled with a suitable water flow rate through the reaction zone.

Following heating of the feedstock components, oxygen is mixed with water which, as a result of preheating and pressurisation, will be under supercritical or near supercritical conditions and hence capable of solubilising the feedstocks. In the embodiment illustrated in FIG. 3, oxygen and water are mixed in premixer 18A. The precursor is also mixed with water in premixer 18B. Of course, the precursor could also be separately premixed with water prior to entry into the preheater 16.

The premixer (or premixers where premixing of each reactant and water is undertaken) may take various forms such as Y, L or T piece, double T configurations or a static mixer, as illustrated in FIGS. 4A, 4B, 4C, 4D and 5 respectively. In FIGS. 4A to 4D and 5, reference A depicts the preheated water supply to the premixer, B depicts the reactant (paraxylene or oxygen) and P depicts the resulting mixed stream. In the double T configuration of FIG. 4D, two mixed streams are produced P1 and P2. These may either be passed through separate continuous flow reactors or be combined into a single stream and then passed through a single continuous flow reactor. An X piece configuration may also be used, as known to those skilled in the art.

It will be appreciated that instead of premixing one or both reactants with water prior to introduction into the reaction zone, the reactants and water may be introduced separately into the reaction zone and mixed within the reaction zone with the aid of some form of mixing arrangement (e.g. a static mixer) whereby substantially all mixing of the components occurs within the reaction zone.

Where a homogeneous catalyst is to be employed in the reaction, the catalyst is added as a solution from source 19 to the premixed oxygen/water stream at the same time as the precursor is added to the premixed oxygen/water stream either immediately prior to entering the reactor or at the beginning of the reactor (i.e. as shown in FIG. 1A).

Figure 1B:
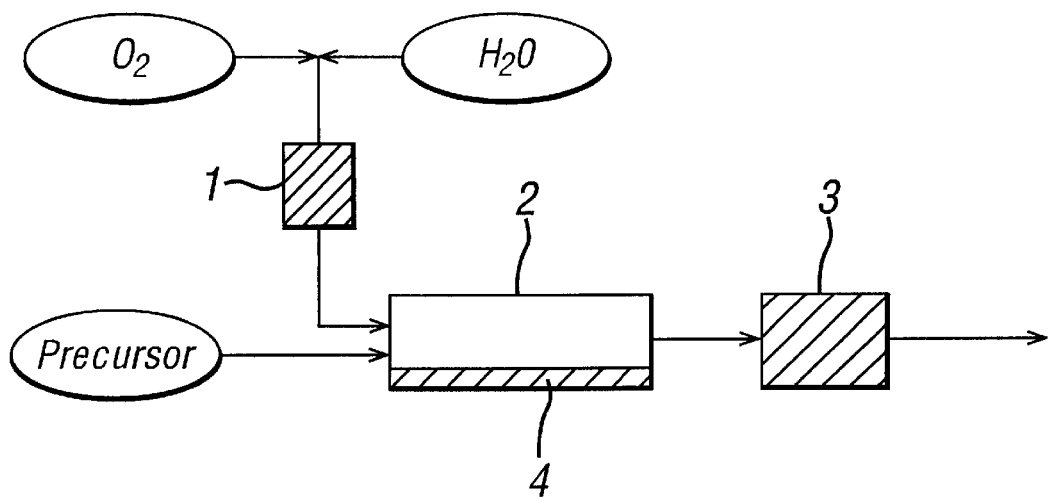

Following preheating and premixing, the feedstock components are combined in a reaction zone 20 to form a single homogeneous fluid phase in which the reactants are brought together. The reaction zone 20 may consist of a simple mixer arrangement in the form of a tubular plug flow reactor, e.g. a pipe of a length which, in conjunction with the flow rate of the combined reactants, provides a suitable reaction time so as to secure conversion of paraxylene to terephthalic acid with high conversion efficiency and low 4-CBA content.

Where the reaction is carried out in the presence of a heterogeneous catalyst system (i.e. as shown in FIG. 1B, the catalyst system may be distributed lengthwise with respect to the flow direction and may be co-extensive with the reaction zone so that, once the supercritical or near supercritical fluid passes beyond the section of the pipe occupied by the catalyst system, the rate of reaction falls significantly to suppress the production of degradation products.

The reactants may be combined in "one shot" upstream of the reactor 20. Alternatively, they may be combined in a progressive manner by injecting one reactant into a stream containing the other reactant at multiple points along the length of the reactor. One way of implementing a multiple injection arrangement is shown in the continuous flow reactor of FIG. 6 in which the reactor is constituted by a pipe P. In an embodiment wherein a premixed oxygen/water stream is added to a premixed precursor/water stream (as shown in FIG. 2D) a premixed paraxylene/supercritical or near supercritical water stream W is supplied to the upstream end of pipe P. For a process in which homogeneous catalysts are used, water stream W would also contain the catalyst; in a process using heterogeneous catalysts, the catalysts would be present inside pipe P. The stream passes through the reactor pipe P and at a series of locations spaced at intervals along the length of the pipe P, preheated and compressed oxygen dissolved in supercritical or near supercritical water is supplied via injection passages A to E to produce a product stream S comprising terephthalic acid in supercritical or near supercritical aqueous solution. In this manner, the oxygen necessary to effect complete oxidation of paraxylene to terephthalic acid is injected progressively with the aim of controlling oxidation and minimising side reactions and possible burning of paraxylene, terephthalic acid or terephthalic acid intermediates.

Referring now back to FIG. 3, following the reaction to the desired degree, the supercritical or near supercritical fluid is passed through a heat exchanger 22 through which heat exchange fluid is circulated via closed loop 24 so that heat can be recovered for use in the preheater 16. One scheme (not shown) for post-reaction cooling of the terephthalic acid solution involves the use of heat exchanger networks to cool the stream to subcritical temperatures, e.g. of the order of 300° C. to retain the terephthalic acid product in solution and thereby avoid the risk of fouling of heat exchange surfaces, followed by use of a train of flashing crystallisers (similar to those employed in conventional terephthalic acid purification by hydrogenation) to cool and precipitate the terephthalic acid product.

The cooled solution is then supplied to a product recovery section 26 in which the terephthalic acid is precipitated from the solution. Any suitable method of product recovery known to those skilled in the art may be used. The product recovery section 26 may comprise one or more stages of cooling or evaporative crystallisation to crystallise the terephthalic acid to form a slurry of terephthalic acid crystals in aqueous mother liquor. Where the product recovery section 26 comprises one or more flashing crystallisers, the resulting flash streams from the crystallisers may be used to preheat the inlet water and paraxylene streams to the reactor, either indirectly via conventional heat exchangers or via direct injection of the flash into the water and/or paraxylene feeds to the reactor. The slurry obtained following crystallisation may be subjected to a solids-liquid separation process using for example filtration devices operating under superatmospheric, atmospheric or sub-atmospheric conditions, with or without washing facilities, such as described in prior published International Patent Applications Nos. WO-A-93/24440 and WO-A-94/17982 (the disclosures of which are incorporated herein by this reference). Thus, for example the integrated solids separation and water washing apparatus may comprise a belt filter unit, or a rotary cylindrical filter unit operated with the slurry side, or a drum filter unit (e.g. a BHS-Fest pressure filter drum formed with a plurality of slurry receiving cells in which the mother liquor is displaced from filter cake by water under hydraulic pressure supplied to the cells). After filtering the slurry, the recovered terephthalic acid may be used directly for the production of polyester, for instance, for packaging, such as bottles, or fibres. Similarly it can be dried. If not already at atmospheric pressure, the filter cake of terephthalic acid may be transferred to a low pressure zone (e.g. atmospheric pressure) for drying via a suitable pressure letdown device such as a lock hopper arrangement, a rotary valve, a ram-type pump, a screw feed device or a progressive feed device such as a progressive cavity pump of the type used to pump cold pastes of high solids contents.

The temperature of separation and the level of washing required will be dependent on the levels of impurities generated in the reaction, the means of recovering the product and the required product specification. Although in general, it will be desirable to produce terephthalic acid which is sufficiently pure to render further purification unnecessary (e.g. by oxidation and/or hydrogenation of an aqueous solution of the terephthalic acid to convert 4-CBA to terephthalic acid or to paratoluic acid, as the case may be), we do not exclude the possibility of carrying out such purification subsequent to the supercritical or near supercritical water oxidation of paraxylene.

Following recovery of the aromatic carboxylic acid product, at least part of the aqueous mother liquor (including soluble catalyst components if homogeneous catalysis is employed in the oxidation reaction) may be recycled for reuse in the oxidation reaction, e.g. by admixture with fresh water and/or the reactants. However, if the recycled mother liquor contains catalyst components, it should not be added to the O₂/water stream prior to addition of precursor. The amount recycled will usually be a major fraction of the recovered mother liquor, with a purge being taken in order to reduce standing concentrations of by-products in the process. The purge stream may be treated to recover its catalyst content where applicable and its organic content.

Figure 7:
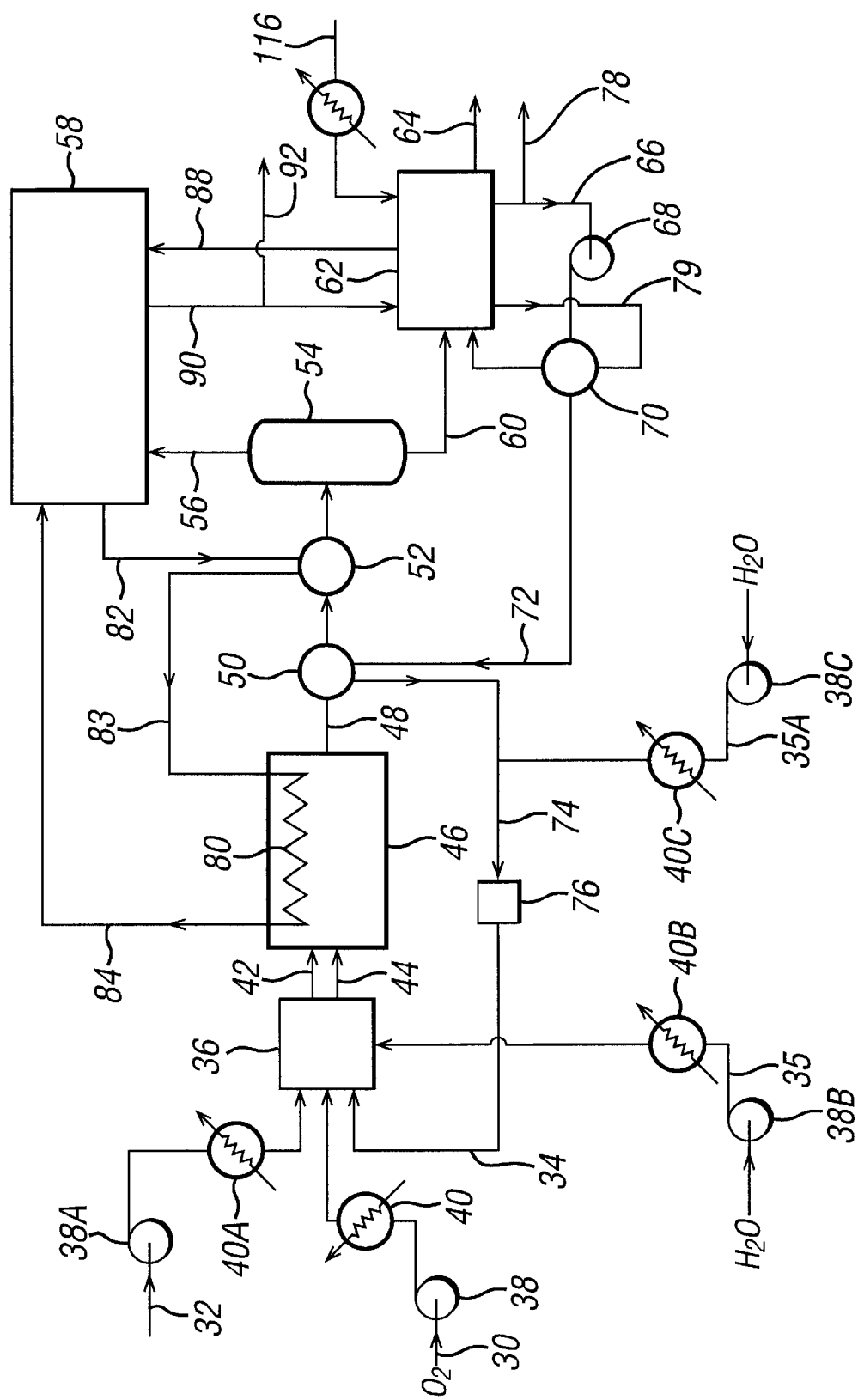
FIGS. 7 and 8 are schematic flowsheets illustrating mother liquor recycle and heat removal from a reactor for use in oxidising a terephthalic acid precursor in supercritical or near supercritical water, substantially pure oxygen being used as the oxidant in the embodiment of FIG. 7, and air being the oxidant in the embodiment of FIG. 8.

Referring now to FIG. 7, in this embodiment liquid oxygen (line 30), liquid paraxylene (line 32) and water (line 34) are supplied to a mixing unit 36. The oxygen and paraxylene supplies are pressurised by pumps 38, 38A and heated to elevated temperature, for example by high pressure steam, in heat exchangers 40, 40A. The mixing unit 36 is configured to mix the reactants with the water supply to produce two streams 42, 44, one stream comprising a water/paraxylene mixture and the other stream comprising oxygen dissolved in water, which are fed to a continous flow reactor 46 in the form of a pipe in which the streams are mixed, e.g. by an unshown static mixing arrangement within the pipe, to initiate the reaction. FIG. 7 is intended primarily to illustrate the arrangement for a system in which a heterogeneous catalyst is employed. For such processes in which a heterogeneous catalyst is utilised, the solid catalyst as a porous medium, a fixed bed or other arrangement, as herein described, may be contained within the flow volume of the reactor 46. For processes in which a homogeneous catalyst is utilised, the catalyst as a solution in water may be added either into the paraxylene/water stream 42 immediately prior to entering the reactor, or on combination of streams 42 and 44 at the beginning of or immediately before the reactor, using rapid mixing, for example by the use of a static mixer or similar device.

The supply of fresh make-up water to the system may be effected at various points. One of the most convenient points is upstream of the main pressurisation pump 68, for instance via line 116 which is described in more detail below in relation to FIG. 8. Water may also be fed after pressurisation in pump 38C and heating in heat exchanger 40C via line 35A into line 74, or prior to the exchangers (50,70). Alternatively, water may be fed, after pressurisation in pump 38B and heating in heat exchanger 40B independently into the preheater 36 via line 35.

Following reaction under supercritical or near supercritical conditions, the product stream 48 in the form of a solution of terephthalic acid (plus small amounts of unreacted reactants, intermediates etc) is cooled by passage through heat exchangers 50 and 52 and may be optionally flashed down to a lower pressure and temperature in flash vessel 54. The means of effecting such a step at this point or in the product recovery section 62 may involve known devices, singly or in multiples, but should be configured to avoid deposition of solids, by means such as localised heating, as known to those skilled in the art. Thus, as the stream from reactor 46 is passed through heat exchangers 50 and 52, the temperature of the stream is monitored and controlled so that the product does not precipitate; precipitation should not occur until flash vessel 54. A substantial amount of steam and some gaseous components such as nitrogen, oxygen, carbon oxides are supplied via line 56 to an energy recovery system 58 while the terephthalic acid solution is supplied via line 60 to a product recovery section 62.

In the product recovery section, the solution of terephthalic acid is processed through a multi-stage crystallisation train in which pressure and temperature are progressively lowered to crystallise the terephthalic acid product in crystal form. The product of the crystallisation process is a slurry of terephthalic acid crystals in an aqueous mother liquor. After the final crystallisation stage, the slurry may be at any desired pressure, e.g. atmospheric pressure or above. The slurry is then subjected to a solids-liquid separation of any suitable form to separate the crystals from the mother liquor. The solids-liquid separation may be carried out using any device suitable for this purpose and arranged to operate under elevated pressure conditions or at atmospheric pressure depending on the pressure following the final crystallisation stage. As referred to previously, the solids-liquid separation can be carried out using an integrated solids separation and water washing apparatus such as a belt filter unit, a rotary cylindrical filter unit, or a drum filter unit (e.g. a BHS-Fest filter drum formed with a plurality of slurry receiving cells in which the mother liquor is displaced from filter cake by water under hydraulic pressure supplied to the cells).

In FIG. 7, the terephthalic acid crystals recovered are supplied via line 64 to a drier (not shown) or to the direct production of polyester. Where the solids-liquid separation is carried out under elevated pressure conditions, the crystals are conveniently let down to atmospheric pressure using a suitable device (e.g. as disclosed in International Patent Application No. WO-A-95/19355 or U.S. Pat. No. 5,470,473) before being transferred to drying equipment. The mother liquor from the solids-liquid separation is recovered via line 66, repressurised by pump 68 and recycled to the mixer unit 36 via heat exchanger 70, line 72, heat exchanger 50, line 74, start-up/trim heater 76 and line 34. Thus, under steady state operating conditions, the recycled mother liquor may contribute to the source of water for supply to the reactor 46 as well as a vehicle for the recycle of catalyst to the process, especially where the oxidation process uses a homogeneous catalyst system. The mixture unit 36 is configured such that, where the recycled mother liquor may contain catalyst, i.e. homogeneous catalyst, the recycled mother liquor is mixed with the paraxylene stream rather than the oxidant stream since according to the process of the present invention the addition of catalyst to oxidant should be contemporaneous with the addition of precursor to oxidant. Thus, where the recycled mother liquor contains catalyst, the mixture unit is configured such that the oxidant stream 30 may be mixed with fresh water from line 35.

Because water is generated in the course of the reaction, a water purge is taken from the system. This may be effected in several ways; for instance, the purge may be taken via line 78 or from a suitable flash condensate (for example as will be described below in connection with the energy recovery system). The latter may be more advantageous as it will be somewhat less contaminated with organics than a purge from the mother liquor recovered via line 66. The purge however recovered may be passed to effluent treatment, e.g. aerobic and/or anaerobic processing.

In the heat exchanger 70, the temperature of the mother liquor is increased by about 30 to 100° C., through heat transfer from steam flashed from one or more of the crystallisation stages, e.g. the first stage highest pressure and temperature crystalliser vessel. The flash (line 79) used for this purpose may, following passage through the heat exchanger 70, be returned as condensate to the product recovery section for use as wash water in washing the terephthalic acid filter cake produced by solids-liquid separation. In the heat exchanger 50, the temperature of the mother liquor is increased still further, for instance by about 100 to 200° C., as a result of heat transfer from the high temperature product stream 48 from the reactor 46. In this manner, the product stream is subjected to cooling while significantly increasing the temperature of the mother liquor recycle stream. The trim/start-up heater 76 serves to boost the temperature of the mother liquor recycle stream, if necessary, to secure supercritical or near supercritical conditions. Under steady state operation of the process such boost may be optional since the mother liquor may be rendered supercritical or near supercritical following passage through the heat exchanger 50. The heater 76 may not therefore be necessary under steady state conditions and may be deployed purely for start-up operation, initially using pressurised water from a source other than mother liquor. In this embodiment, the water solvent is rendered supercritical or near supercritical prior to mixing with one or both reactants. However, it will be understood that raising of the temperature to secure the desired supercritical or near supercritical conditions may be effected prior to, during and/or following the mixing stage.

In the embodiment of FIG. 7, the heat of reaction generated in the course of reacting the precursor with oxygen is removed at least in part by heat exchange with a heat-accepting fluid, preferably water, which is passed through the interior of the reactor 46 by means of a coiled tube 80 or a series of generally parallel tubes (as in a tube in shell heat exchanger design) or the like. The water employed is pressurised and heated to a temperature sufficiently high that, at the external surface of the conduit or conduits 80 conducting the water through the reactor, localised cooling which could otherwise cause precipitation of components, such as terephthalic acid, in the reaction medium is avoided. The water for this purpose is derived from the energy recovery system 58. Thus, in FIG. 7, water at elevated pressure and temperature is supplied via line 82 to heat exchanger 52 where it is used to cool the product stream further following passage through the heat exchanger 50. The water then passes via line 83 through the conduit(s) 80 with consequent raising of high pressure, high temperature steam which is fed to the energy recovery system 58 via line 84.

The energy recovery system 58 is also supplied with steam flashed from one or more stages of the crystallisation train. This is depicted by line 88. This steam may for example be used to preheat the water supplied via line 82 to the heat transfer conduit(s) 80. Condensate resulting from processing of the steam feeds supplied to the energy recovery system 58 may be passed via line 90 to the product recovery section for use for example in washing the terephthalic acid filter cake produced in the solids-liquid separation. A water purge 92 may be taken from line 90 if desired, with the advantage that a purge taken at this point will be less contaminated than a purge taken from the mother liquor via line 78.

In FIG. 7, (which, as noted above, is primarily intended to illustrate a process utilising a heterogeneous, as opposed to a homogeneous catalyst) the reactant(s) are shown as being introduced into the recycled mother liquor after the mother liquor has been heated by heat exchange with the product stream in heat exchanger 50. In a modification, a reactant may be admixed with the mother liquor recycle stream upstream of the heat exchange with the product stream. Where both reactants are so admixed with the mother liquor recycle stream, the latter is split into separate streams with which the reactants are respectively admixed so that the reactants are maintained isolated from each other until brought together for reaction. It will also be understood that the embodiment of FIG. 7 may be modified in the manner indicated in FIG. 6 by introducing one or even both of the reactants via multiple injection points along the flow path of the reaction medium so that the one or both reactants are introduced to the reaction progressively.

In the energy recovery system 58, various heat recovery processes may be carried out in order to render the process energy efficient. For instance, the high pressure steam raised following passage of water through the conduit(s) 80 may be superheated in a furnace supplied with combustible fuel and the superheated steam may then be passed through one or more steam condensing turbine stages to recover power. Part of the high pressure steam may be diverted for use in preheating the reactants (heat exchangers 40, 40A and 40B) or for preheating stream 82 where this is necessary to effect a system of high thermal efficiency. The condensed water recovered from the turbine stages and from the heat exchangers 40, 40A and 40B may then be passed through a train of heating stages in order to preheat the water for recirculation to the reactor 46 via heat exchanger 52 thus forming a closed loop with make-up water being added as needed. The heating stages typically comprise a cascade of heat exchangers by means of which the recirculating water flow returning to the reactor 46 is progressively raised in temperature. In some heating stages, the heat-donating fluid may be constituted by the flash steam derived at different pressures and temperatures from different stages of the crystallisation train. In other heating stages, the heat-donating fluid may be combustion gases rising in the furnace stack associated with the furnace used to superheat the high pressure steam supplied via line 84.

Figure 8:
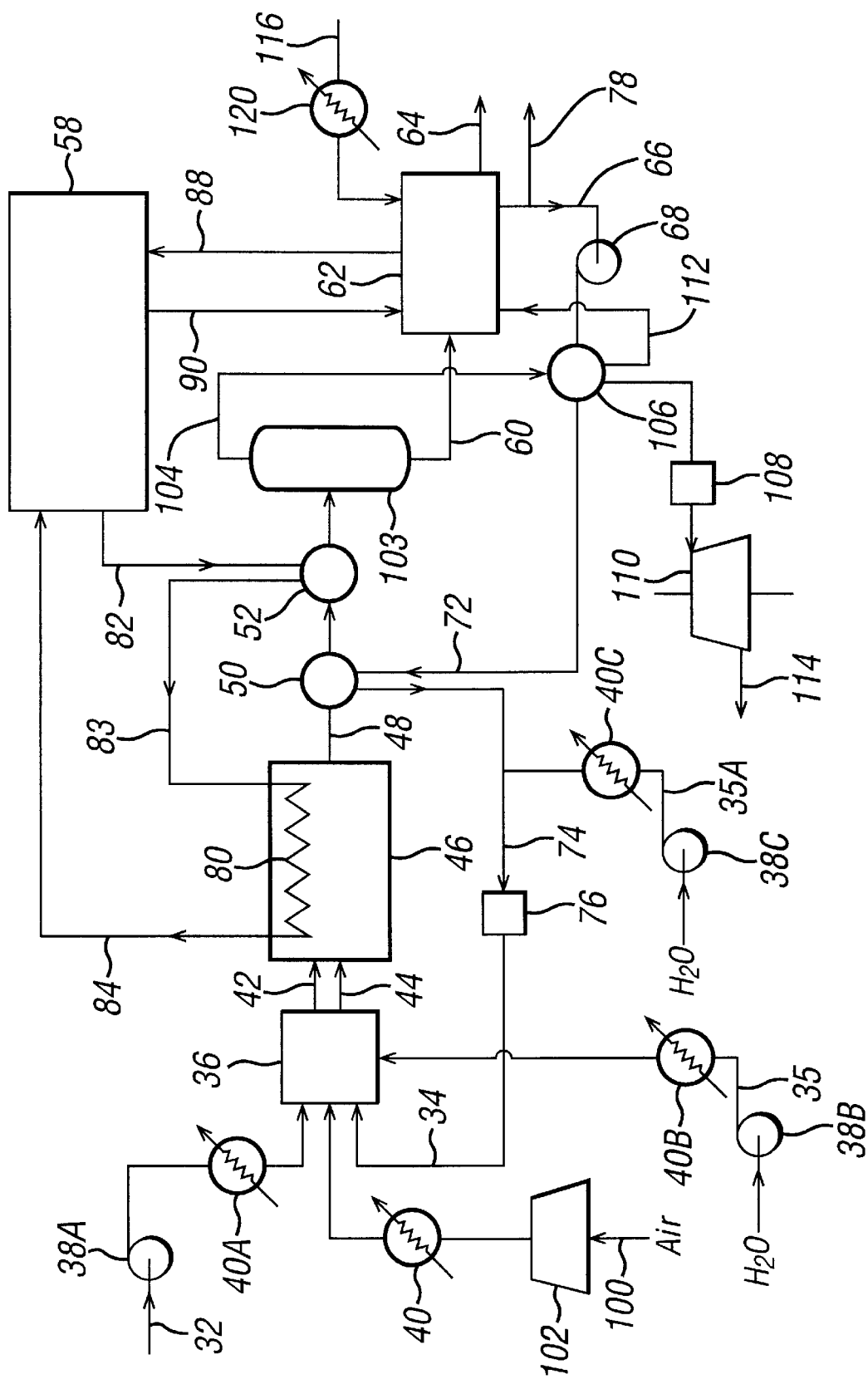

The embodiment of FIG. 7 employs substantially pure oxygen as the oxidant. FIG. 8 illustrates a similar embodiment to that of FIG. 7 but using a supply of compressed air (which may be oxygen enriched) as the oxidant. The embodiment of FIG. 8 is generally similar to that of FIG. 7 and those parts which function in generally the same way are depicted by the same reference numerals in both Figures and will not be described further below unless the context requires otherwise. As shown, the air supply 100 is supplied via an air compressor 102. As a result of using air, a substantial amount of nitrogen is introduced into the process and must therefore be appropriately handled. In this case, the product stream following passage through the heat exchangers 50 and 52 is flashed down in flash vessel 103 to a lower temperature to condense water to a greater extent than in the embodiment of FIG. 7 thereby reducing the water content of the overheads. As described in relation to FIG. 7, temperature of the product stream through the heat exchangers 50 and 52 is controlled such that precipitation of product occurs only in flash vessel 103. The overheads stream is supplied via line 104, heat exchanger 106 and fuel-fired heater 108 to a gas turbine 110. The overheads stream is passed through heat exchanger 106 in order to transfer heat to the mother liquor recycle stream while knocking out further water which can be passed to the product recovery section 62 via line 112 for use, for example, as wash water. For reasons of energy efficiency, it is desirable to heat the gaseous overheads stream high temperature before introduction into the turbine 110, hence the reason for heating the overheads stream by means of heater 108. There may be more than one gas turbine stage, in which case the overheads stream will be heated to an elevated temperature upstream of each such turbine stage. Line 114 depicts the overheads stream exiting the turbine 110 at low pressure and temperature. Where the oxidation process leads to the generation of species such as carbon monoxide etc. which are undesirable, for example for corrosion and/or environmental reasons, provision may be made for treating the overheads stream to reduce/eliminate such components before or after passage through the turbine 110 and/or discharge. Such treatment may comprise subjecting the overheads stream to catalytic combustion and/or scrubbing with a suitable reagent, e.g. an alkaline scrubbing liquor. The turbine 110 may be mechanically coupled with the air compressor so that the latter is driven by the turbine.

In the embodiment of FIG. 8, water exits the system via the overheads stream. At least part of this water may be recovered if desired and recirculated for use for example as wash water in the product recovery section 62. Alternatively or additionally, make-up water may be supplied via line 116 to the product recovery section to compensate for the water lost in handling the large volumes of nitrogen as a result of compressed air usage. Such make-up water may be preheated and used as wash water, preheating being effected for example by diverting part of the flash streams (collectively depicted by reference numeral 88) via line 118 to heat exchanger 120 and returning the water condensed from the flash stream to the product recovery section 62 as wash water.

Although the invention has been described mainly with reference to paraxylene as the terephthalic acid precursor, it will be appreciated that other precursors may be employed instead or in addition to paraxylene, e.g. 4-tolualdehyde and 4-toluic acid. Also it will be appreciated that the invention is applicable to the production of other aromatic carboxylic acids such as isophthalic acid.

EXAMPLES

Figure 9:
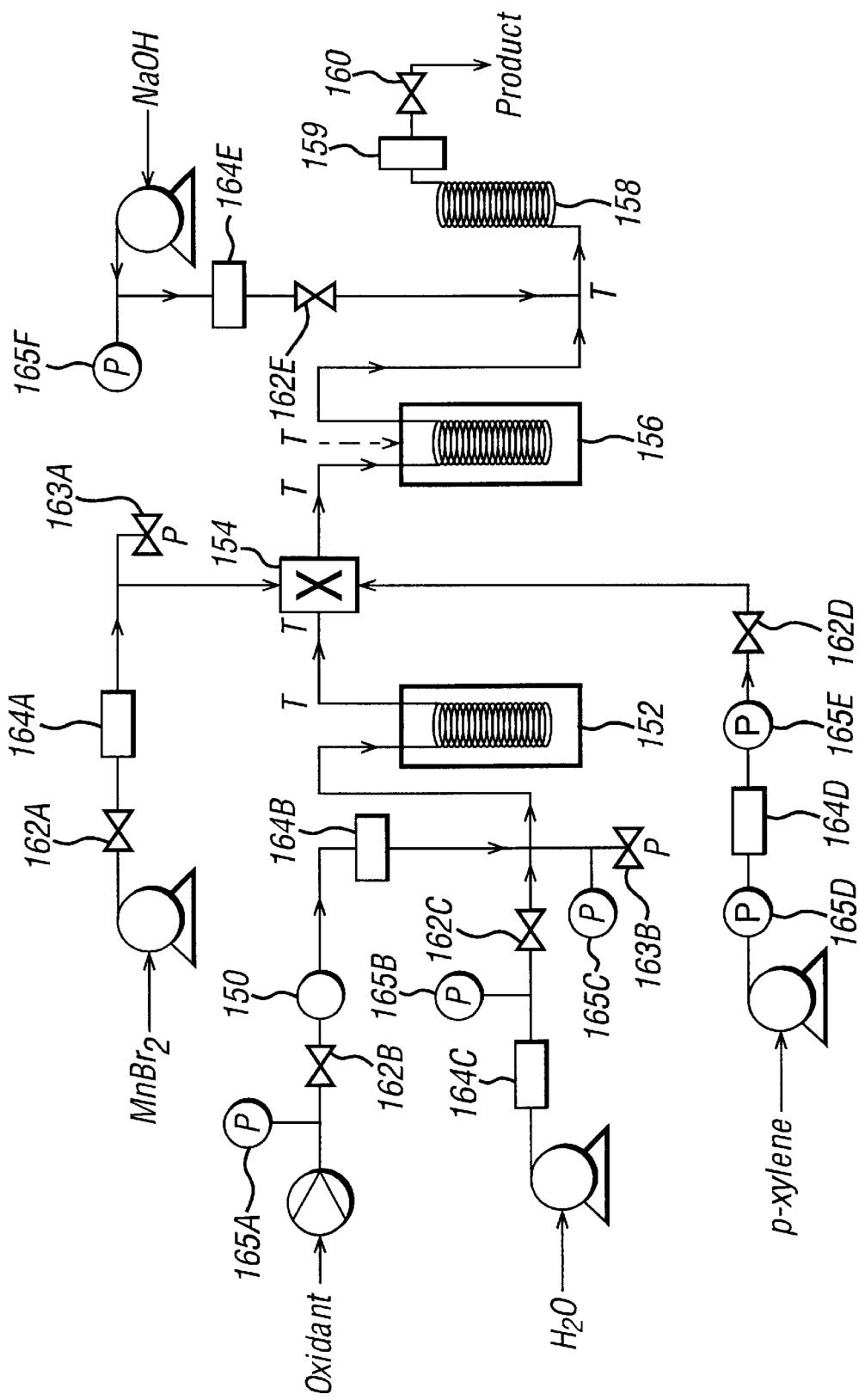
FIG. 9 is a schematic flowsheet of the system used in the laboratory scale experiments described in the Examples.

Experimental work was carried out on a laboratory scale by the continuous oxidation of para-xylene by $O_2$ in supercritical water at about 375 to 420° C. and 240 to 280 Bara with $MnBr_2$ catalyst. The exotherm was minimised by using relatively dilute solutions (<5% organic w/w). The experiments provided yields of terephthalic acid about 90%. The basic configuration of the system is as set out in FIG. 1A. A more detailed illustration of the system used in these laboratory scale experiments is shown in FIG. 9.

Oxygen was fed using either of two different schemes. In the first, oxygen gas was compressed into a dosage unit 150 from which pulses of $O_2$ gas were fed into a mixing piece where it was mixed with cold water. Alternatively, hydrogen peroxide (100 volume) was fed to a pump, cooled to 5° C. or less, feeding into a mixing piece where it was mixed with cold water.

The $O_2$/water was then heated in preheater 152 consisting of a 6 m coil of ¼ inch O.D. stainless steel tubing cast into an aluminium block. Adequate mixing of oxygen and water was achieved by using a relatively long coil in the preheater 152. The $O_2$/water fluid was then passed through the cross piece 154, where it was contacted with the para-xylene and solution of $MnBr_2$ catalyst, fed in from their own pumps. The reaction mixture was passed through reactor 156, similar to the Preheater 152.

Terephthalic acid (TA) precipitates easily from hot solutions as they cool, and the suspended TA can cause frequent blockages in apparatus of this scale. Therefore, cold NaOH at greater than excess was injected into the product stream from the reactor 156 to ensure that all TA was in the form of the freely soluble disodium terephthalate salt. The solution was then passed through cooling device 158, filter 159 and back-pressure regulator 160. TA was subsequently recovered by acidification of the collected solution, once it had cooled. NaOH may not be needed in a larger scale apparatus, where increased dimensions reduce the problems of blockages.

Other components are labeled in FIG. 9 as follows: 162 A–E: valves; 163 A–B: pressure release valves; 164 A–E: non—return valves; 165 A–F pressure transducers; T: thermocouple (the aluminium block heaters of preheater 152 and reactor 156 also contain thermocouples, not shown). The $O_2$ compressor, dosage unit, preheater and reactor were obtained from NWA GmbH; the pumps were Gilson 302, 305, 306 and 303; the back-pressure regulator obtained from Tescom (model 26-1722-24-090).

Maximum corrosion occurs in the region of the cross-piece 154, where $O_2$, paraxylene and the catalyst solution meet, particularly at the incoming, unheated catalyst feed pipe where a high temperature gradient coincides with bromide ions. Hastelloy (or titanium) was used for the final section of the catalyst feed pipe and downstream of the reactor, before the mixer section for addition of NaOH solution where a temperature gradient of approximately 100° C. occurs over a length of approximately 5 cm, and stainless steel for the other components. All pipe work liable to corrosive failure is protected inside wider bore stainless steel pressure tubing to contain any inadvertent leaks.

Before each run the apparatus was hydrostatically tested when cold and then heated with a flow of pure water (5–10 ml per minute). Once the operating temperature was reached, the $O_2$ feed and the pumps for para-xylene, $MnBr_2$ and NaOH were started. Typically, an experiment was run for 4–5 hours. The products were usually collected for sequential periods of 30–60 minutes and analysed. A weighed portion of the product solution containing the disodium terephthalate salt was acidified with 2 N HCl (alternatively $H_2SO_4$ or $HNO_3$ could be used) to precipitate the TA and other components. The TA was filtered using a Buchner funnel, washed with cold water and air dried in a dessicator over dried silica gel and weighed. Purity was verified principally by HPLC. The yield of solid product collected was calculated as a percentage of the total para-xylene pumped into the apparatus converted to TA.

The results in Table 1 demonstrate that high selectivity for the oxidation of para-xylene to terephthalic acid (TA) can be achieved, depending on the conditions, mixing and concentrations of each reactant. The yield is highly sensitive to a range of variables, including para-xylene:$O_2$, reactor residence time, para-xylene:catalyst and reactor temperature.

Para-xylene oxidation intermediates analysed were 4-carboxy-benzaldehyde (4-CBA) and para-toluic acid (p-Tol). In addition, by-products were measured, including 2,6 dicarboxyfluorenone (DCF), iso-phthalic acid (IPA), benzoic acid (BA), benzene 1,2,4 tricarboxylic acid (TMA), 2,4',5-tricarboxybiphenyl (BPTC), diphenic acid, 4,4'-dicarboxybenzophenone (DCBBP), 2,6-dicarboxyfluorenone, 2,6 dicarboxyanthraquinone, 2,6-dicarboxyfluorene and 2,6-dicarboxyanthracene.

HPLC analysis was carried out by direct injection of the recovered solution onto the column. Gradient elution with solvents acetonitrile (16.7%) and buffer (83.3 to 60% and back to 83.3%) was used. The stock buffer solution was prepared by dissolving 15 g anhydrous sodium acetate in 250 ml de-ionised water, before adding acetic acid (50%, 100 ml). The pH was adjusted to 3.9±0.01 with 5% acetic acid, before diluting to 500 ml. The dilute buffer was prepared by diluting 30 ml of the stock buffer solution to 500 ml with de-ionised water. The injection volume with needle wash was 1 microlitre. A Waters Xterra reverse phase column was used, maintained at 40° C. A flowrate of 0.7 ml/min was used and a run time of 14 minutes. A UV detector, operating at 230 nm was used to analyse the peaks.

Example 1

Using 100 volume of hydrogen peroxide, a dilute stock solution was prepared using 56 ml of peroxide and 760 ml of nanopure water (18.3 megohm resistance). A dilute catalyst stock solution was prepared by dissolving manganese bromide in nanopure water to a concentration of 5000 ppm w/w of Br. Para-xylene was held separately undiluted. A stock solution of sodium hydroxide (0.5M) was prepared to feed downstream of the reactor, but before the back-pressure regulator.

De-ionised water alone was pumped through the preheater, mixing-piece, reactor, caustic mixer, cooler and back-pressure regulator at a rate to control the final residence time through the reactor to 65 seconds. The residence time was defined as the volume of the tubular reactor, pipework and fittings between the mixing pieces; the first to mix the reactants to initiate the reaction and the second to quench the reaction with the addition of sodium hydroxide, divided by the volumetric flowrate. The volumetric flowrate was based on the physical properties of water at the mixing conditions, as published in International Steam Tables and by U.S. National Institute of Standards and Technology.

between 26 and 37% w/w. The TA composition in each sample varied slightly and para-xylene oxidation intermediates were detected in each sample. Results are summarised in Table 1.

Example 2

To test the effect of increasing reactor residence time an experiment was run, as in Example 1, at 250 Bar and 400° C. reactor temperature, but with a reactor residence time of 130 seconds and a slightly increased flow of oxygen. This resulted in a reduced yield and poorer selectivity for TA of 9.3 to 21.3% through the run. A reduction in para-xylene oxidation intermediates occurred and reaction by-products were reduced. A higher concentration of benzoic acid resulted.

TABLE 1

Summary Table of Experimental Conditions and Results

| | Reactor conditions | | | Feeds | | | Results for Solid product | | | | | |
|---|---|---|---|---|---|---|---|---|---|---|---|---|
| Ex. | Res. Time Mins | P Bar | T ° C. | p-X‡ % | O₂† % | Catalyst ppm | Yield % | TA % | 4-CBA % | p-Tol % | BA % | By-prods. % |
| 1 | 1.09 | 250 | 400 | 0.58 | 87–93 | 1632 | 26–37 | 12.9–25.5 | 8.0–22.4 | 14.4–40.8 | 1.4–5.2 | 1.1–2.9 |
| 2 | 2.17 | 250 | 400 | 0.58 | 111 | 1632 | 13–30 | 9.3–21.3 | 0–1.6 | 5.9–12.0 | 4.9–7.9 | 0–0.9 |
| 3 | 2.08 | 250 | 350 | 0.7 | 120 | 975 | 45–61 | 45.3–61.2 | 3.2 | 6.58–17.6 | 6.2–9.8 | 0 |
| 4 | 12.8 | 250 | 300 | 0.58 | 149 | 537 | 0 | 0.1–0.4 | 0 | 0 | 0 | 0.1 |
| 5 | 12.8 | 250 | 250 | 0.58 | 149 | 537 | 0 | 0–0.3 | 0 | 0–0.14 | 0 | 0.2–1.2 |
| 6 | 11.7 | 250 | 200 | 0.58 | 149 | 537 | 0 | 0 | 0 | 0–13.9 | 0 | 0–1.2 |
| 7 | 0.54 | 250 | 400 | 0.58 | 115 | 1632 | 71 | 51.9–63.8 | 0 | 5.95 | 5.9–11.8 | 0–1.6 |
| 8 | 2.42 | 250 | 300 | 0.58 | 45 | 1632 | 13–98 | 13.0–26.4 | 8.5–11.5 | 35.4–64.1 | 2.4–3.7 | 4.3–5.6 |
| 9 | 2.43 | 250 | 300 | 0.58 | 178 | 1632 | 42–81 | 71.6–81.8 | 0 | 0 | 4.9–7.1 | 0 |
| 10 | 0.3 | 250 | 400* | 0.58 | 120 | 1640 | 72–100 | 91.8–94.1 | 0 | 0 | 5.8–8.2 | 0 |
| 11 | 0.3 | 250 | 400* | 1.5 | 180 | 1640 | 69–95 | 92.1–93.8 | 0 | 0 | 6.3–8.0 | 0 |
| 12 | 0.15 | 250 | 400* | 1.5 | 180 | 1640 | 74–90 | 93.5–95.3 | 0 | 0 | 4.7–6.5 | 0 |
| 13 | 0.15 | 250 | 400* | 2 | 120 | 1640 | 79–85 | 93.9–95.1 | 0 | 0 | 4.9–6.1 | 0 |

‡para-xylene concentration in reactor (w/w)
†as proportion of stoichiometry for full conversion of p-X to TA
* Temperature at mixing piece, following change of reactor to short length of pipe The back-pressure regulator was set to control the reactor pressure at 250 Bar. The heaters were set to control the mixing piece at 385° C. and the reactor at 400° C.

Each of the reactants was pumped separately to the mixing piece, as shown in FIG. 9. Para-xylene was fed at a concentration of 0.58% w/w to the reactor, oxygen was fed at close to stoichiometric rates, for the oxidation of para-xylene to terephthalic acid and catalyst solution was fed to the mixing piece to generate a concentration of 1632 ppm Br in the reactor.

After reaching stable setpoint conditions samples were collected over a 30 to 60 minute interval and subsequently analysed. This experiment was run for 3.5 hours. The results showed a variation in solid yield for the samples collected Example 3

Reducing temperature was tested by running an experiment, as in Example 1, at 250 Bar, 350° C. reactor temperature and a reactor residence time of 125 seconds. A slightly reduced catalyst concentration of 975 ppm Br and an increase in oxygen level resulted in a significant yield with moderate selectivity for TA. Despite conditions being sub-critical for water, these results show a similar result to those at super-critical conditions in example 1. By-products were further reduced in comparison with example 2.

Example 4

An experiment was run, as in Example 3, at 250 Bar and 300° C. reactor temperature to evaluate the effect of subcritical temperature. A reduced catalyst concentration of 537 ppm Br was used and despite increasing the relative oxygen concentration and extending the reactor residence time to over 11 minutes no solid product resulted from the normal work-up of the sample. Analytical results showed only minor conversion of the para-xylene fed.

Example 5

An experiment was run, as in Example 4, but at a still lower temperature of 250° C. reactor temperature and 250 Bar. No solid product resulted from the normal work-up of the sample, as in Example 4. Analytical results showed only minor conversion of the para-xylene fed.

Example 6

An experiment was run, as in Example 5, but at a still lower temperature of 200° C. reactor temperature and 250 Bar. No solid product resulted from the normal work-up of the sample, as in Examples 4 and 5. Analytical results showed only minor conversion of the para-xylene fed.

Example 7

To explore the effect of reactor residence time an experiment was run, as in Example 1, at 250 Bar and 400° C. reactor temperature, with a reactor residence time estimated at 32 seconds. Oxygen stoichiometry for the total conversion of para-xylene was above parity, giving an increase in yield of solid products together with a relative increase in selectivity for TA due to the reduction in 4-CBA, p-Tol and by-products produced. An increase in BA generation appears to follow the increase in TA selectivity.

Example 8

To explore the effect of reactor residence time, oxygen stoichiometry and catalyst concentration an experiment was run, as in Example 4, at 250 Bar, 300° C. reactor temperature (varied between 296 and 324° C.) and a reactor residence time of approximately 145 seconds. A reduced oxygen level was used and the temperature was sub-critical for water. The catalyst concentration of 1632 ppm Br was used to improve the extent of reaction, however, low conversion resulted through the run and only moderate selectivity for TA occurred. Oxidation intermediates and by-products were all detected by analysis, showing the necessity to maintain sufficient catalyst in the reactor to promote the selective oxidation of para-xylene.

Example 9

To confirm the effect of oxygen stoichiometry an experiment was run, as in example 8, at 250 Bar, 300° C. reactor temperature and a reactor residence time of approximately 145 seconds. An enhanced oxygen concentration was used, significantly greater than required for the full conversion of para-xylene to TA. The mixing piece was maintained at 378° C., but the reactor temperature was sub-critical for water. A catalyst concentration of 1632 ppm Br was used. Analysis of the product indicates a good selectivity for TA and no oxidation intermediates of para-xylene or by-products were detected. A significant concentration of benzoic acid is the only other component detected in the solid product. The results demonstrate the requirement to maintain oxygen stoichiometry for full para-xylene oxidation.

Example 10

An experiment was run, as in Example 1, at 250 Bar and 400° C. reactor temperature, with a reduced reactor residence time, estimated at approximately 20 seconds. The reduced reactor residence time was achieved by using a shorter length of pipe, rather than a coiled, heated pipe. An oxygen concentration, greater than required for the full conversion of para-xylene to TA and a catalyst concentration of 1640 ppm Br was used. Analysis of the product indicates a high selectivity for TA and no oxidation intermediates of para-xylene or by-products were detected. A significant concentration of benzoic acid, corresponding to the loss of selectivity for TA is present in the solid product. In comparison with example 9 the results indicate that at short reactor residence times a small oxygen excess only is required to generate high TA yields and selectivity.

Example 11

An experiment was run, as in Example 10, at 250 Bar and 400° C. in the reactor. An increased concentration of para-xylene and a high excess over stoichiometry of oxygen was fed to the mixing piece. A catalyst concentration of 1640 ppm Br was used. Separate samples were collected for 15 minutes and analysis of the product indicated a similar selectivity for TA and no oxidation intermediates of para-xylene or by-products. Benzoic acid was again the only other component detected, but at reduced levels compared with example 10.

Example 12

An experiment was run, as in example 10, at 250 Bar and 400° C. reactor temperature, with a reactor residence time, estimated at approximately 10 seconds. The shorter reactor residence time was achieved by using increased flowrates of the reactants. Analysis of the product indicates a high selectivity for TA. A slightly lower concentration of benzoic acid was detected in the solid product compared with example 10, probably due to the lower reactor residence time. No oxidation intermediates of para-xylene or other by-products were measured in the solid product.

Example 13

Limited by control of the reactor temperature, due to the highly exothermic reactions taking place, the substrate concentration was increased further. An experiment was run, as in Example 12, at 250 Bar and 400° C. reactor temperature with an increase in para-xylene concentration to 2%, with an excess of oxygen over stoichiometry. Analysis of the product indicates a high selectivity for TA. A significant concentration of benzoic acid was detected in the solid product and no oxidation intermediates of para-xylene or other by-products.

To confirm the overall mass balance for the experiment additional measurements were carried out. For one particular sample taken over a timed interval of 15 minutes a solid product with a composition of 92.1% w/w TA and 7.9% w/w BA. In this period 0.6814 g of para-xylene was fed to the experimental unit and the solid recovered was 1.009 g. The measured carbon recovery was 97.4%.

Example 14

To confirm the required mixing configuration an experiment was run feeding the catalyst solution at 1000 ppm Br with water containing dissolved oxygen to a preheater at 385° C. and 240 Bar. Para-xylene was fed to the mixing piece to give 1% v/v downstream of the preheater. Oxygen was fed at the stoichiometric requirement for complete conversion of para-xylene to TA. Carbon recovery in the solid product was 22–69% w/w with a TA yield between 11–18%.

Inspection of the preheater showed significant corrosion to the internal surface of the preheater pipework and a black particulate precipitate coating the pipework. Atomic absorbtion and X-ray diffraction showed the solid to be $MnO_2$.

Running under equivalent conditions, but with no oxygen mixed with the catalyst solution prior to feeding the preheater gave full recovery of $MnBr_2$ after the reactor.

What is claimed is:

1. A process for the production of an aromatic carboxylic acid comprising a carboxylic acid moiety that is directly attached to an aromatic ring structure consisting of carbon atoms, said process using an aqueous solvent comprising water under supercritical conditions or near supercritical conditions, wherein said process comprises contacting one or more precursors of the aromatic carboxylic acid with an oxidant that is dissolved in the aqueous solvent, in the presence of a catalyst, within a reaction zone of a continuous flow reactor, further wherein: (a) the solvent and the oxidant form a single homogeneous phase prior to contact with the one or more precursors; and (b) the one or more precursors, the oxidant and the solvent form a homogeneous phase in the reaction zone.

2. The process of claim 1, wherein the oxidant is first contacted with the one or more precursors at the same time that the catalyst is first contacted with the oxidant.

3. The process of claim 1, wherein the one or more precursors, the solvent and oxidant, and the catalyst are contacted in the reaction zone of the reactor for less than 4 minutes.

4. The process of claim 3, wherein at least 98% by weight of the aromatic carboxylic acid produced is maintained in solution during the reaction.

5. The process according to claim 4, wherein the aromatic carboxylic acid following reaction is precipitated from the reaction medium and contains no more than 5000 ppm by weight of aldehyde produced as an intermediate in the course of the reaction.

6. The process as claimed in claim 5, in which the heat of reaction is removed from the reaction by heat exchange with a heat-accepting fluid.

7. The process as claimed in claim 6, in which the heat-accepting fluid is passed through one or more flow passages at least partly surrounding the reaction zone.

8. The process as claimed in claim 6, in which the heat-accepting fluid is passed through one or more flow passages having a wall or walls, the outer surfaces of which are exposed to the reaction medium within the reaction zone.

9. The process as claimed in claim 8, in which the heat-accepting fluid traverses the reaction zone in counter-current and/or co-current relation with the reaction medium flowing through the reaction zone.

10. The process as claimed in claim 9, in which the heat-accepting fluid following heat exchange with the reaction medium is processed to recover thermal, mechanical and/or electrical energy.

11. The process as claimed in claim 10, in which the heat-accepting fluid comprises water and/or steam.

12. The process according to claim 1, wherein the oxidant is introduced to the reaction at two or more locations.

13. The process according to claim 5, in which the precipitate is separated from the mother liquor.

14. The process according to claim 13, in which at least part of the mother liquor is recycled to the reaction zone.

15. The process according to claim 14, in which prior to recycling the same to the reaction zone the mother liquor is preheated by heat exchange with the product stream from the reaction zone.

16. The process as claimed in claim 1, in which the oxidation reaction is carried out in more than one reaction zone.

17. The process as claimed in claim 3, in which the oxidation reaction is carried out in more than one reaction zone.

18. The process of claim 1, wherein the catalyst is in heterogeneous form and wherein the heterogeneous catalyst is located within the reaction zone.

19. The process of claim 1, wherein the catalyst is in homogeneous form and wherein the homogeneous catalyst is introduced to the reaction zone together with the one or more precursors.

20. The process of claim 1, wherein the aromatic carboxylic acid is selected from the group consisting of terephthalic acid, isophthalic acid, trimellitic acid, naphthalene dicarboxylic acid, and benzoic acid.

21. The process of claim 1, wherein the one or more precursors is xylene.

22. The process of claim 1, wherein the oxidant is an oxygen-containing gas.

23. The process of claim 1, wherein the aromatic ring structure is benzene or naphthalene.

24. The process of claim 1, wherein the solvent consists essentially of water.

25. A process for the production of an aromatic carboxylic acid comprising a carboxylic acid moiety that is directly attached to an aromatic ring structure consisting of carbon atoms, said process comprising the step of contacting a solvent, a catalyst, one or more precursors of the aromatic carboxylic acid, and an oxidant within a reaction zone of a continuous flow reactor, wherein: (1) said solvent is an aqueous solvent comprising water under supercritical conditions or near supercritical conditions; (2) the oxidant and the aqueous solvent are a single homogeneous phase prior to contact with the catalyst and the one or more precursors in the reaction zone; (3) the one or more precursors, the oxidant and solvent, and optionally the catalyst, are contacted so that at least the one or more precursors, the oxidant and the solvent form a single homogeneous phase in the reaction zone; and (4) the oxidant is first contacted with the one or more precursors at the same time that the catalyst is first contacted with the oxidant.

26. The process of claim 25, wherein the one or more precursors is xylene.

27. The process of claim 25, wherein the oxidant is an oxygen-containing gas.

28. The process of claim 25, wherein the aromatic ring structure is benzene or naphthalene.

29. The process of claim 25, wherein the solvent consists essentially of water.

30. A process for the production of an aromatic carboxylic acid comprising a carboxylic acid moiety that is directly attached to an aromatic ring structure consisting of carbon atoms, said process using an aqueous solvent comprising water at a temperature of 300 to 480° C. and at a pressure of 40 to 350 bara, wherein said process comprises contacting one or more precursors of the aromatic carboxylic acid with an oxidant that is dissolved in the aqueous solvent, in the presence of a catalyst, within a reaction zone of a continuous flow reactor, further wherein: (a) the solvent and the oxidant form a single homogeneous phase prior to contact with the one or more precursors; and (b) the one or more precursors, the oxidant and the solvent form a homogeneous phase in the reaction zone.

31. The process of claim 30, wherein the aromatic ring structure is benzene or naphthalene and the solvent consists essentially of water.

32. The process of claim 31, wherein the oxidant is an oxygen-containing gas or hydrogen peroxide.

* * * * *